United States Patent [19]
Perez et al.

[11] Patent Number: 5,836,313
[45] Date of Patent: Nov. 17, 1998

[54] METHODS FOR MAKING COMPOSITE HYDROGELS FOR CORNEAL PROSTHESES

[75] Inventors: Edward Perez, Cambridge; David Miller, Brookline; Edward W. Merrill, Belmont, all of Mass.

[73] Assignee: Massachusetts Institute of Technology, Cambridge, Mass.

[21] Appl. No.: 422,149

[22] Filed: Apr. 14, 1995

Related U.S. Application Data

[63] Continuation-in-part of Ser. No. 384,378, Feb. 3, 1995, which is a continuation of Ser. No. 14,812, Feb. 8, 1993, abandoned.

[51] Int. Cl.$^6$ .............................. A61B 19/00; A61F 2/14
[52] U.S. Cl. ............................... 128/898; 623/4; 623/5; 623/901; 156/272.2; 156/60; 156/1
[58] Field of Search .............................. 623/4, 5, 6, 901; 128/898; 606/107; 156/272.2, 60, 1

[56] References Cited

U.S. PATENT DOCUMENTS

| | | | |
|---|---|---|---|
| 4,715,858 | 12/1987 | Lindstrom | 623/5 |
| 4,842,599 | 6/1989 | Bronstein | 623/5 |
| 5,067,961 | 11/1991 | Kelman et al. | 623/5 |
| 5,112,350 | 5/1992 | Civerchia et al. | 606/107 |
| 5,114,627 | 5/1992 | Civerchia | 264/1.1 |
| 5,162,430 | 11/1992 | Rhee et al. | 525/54.1 |
| 5,192,316 | 3/1993 | Ting | 623/5 |
| 5,196,027 | 3/1993 | Thompson et al. | 623/5 |
| 5,213,720 | 5/1993 | Civerchia | 264/1.4 |

OTHER PUBLICATIONS

Perez et al, "Bilayer Composite Hydrogel for Corneal Epithelial Cell Growth" Fall Meeting of Material Research Society, Boston, Massachusetts (1991).

Peiffer et al, "Pathology of Corneal Hydrogel Alloplastic Implants", Ophthalmology, vol. 92, No. 9, (Sep. 1985).

Azar D.T., et al., "Reassembly of the Corneal Epithelial Adhesion Structures Following Human Epikeratoplasty", Archives of Ophthalmology, 109:1279–1284 (1991).

Baier R.E., et al., "Surface Properties Determine Bioadhesive Outcomes: Methods and Results", J. Biomed. Mater. Res., 18:337 (1984).

Brightbill, F.S., "Corneal Surgery: Theory, Tissue, and Technique", The C.V. Mosby Company St Louis, Missouri (1986).

Cardona, H., "Keratoprosthesis", Ophthalmology, 284–299 (1976).

Curtis, A.S.G., et al, "Substrate Hydroxylation and Cell Adhesion", J. Cell. Sci., 86:9 (1986).

Dole, M., "The Radiation Chemistry of Macromolecules", Academic Press, New York (1972).

Franzblau, C. et al., "Cell Growth on Collagen–HEMA Hydrogels", id., 191–208.

Geggel. H.S., "Collagen Gels for Ocular Surface", Reports Invest. Ophthal. Vis. Sci., 26:901–905 (1985).

(List continued on next page.)

Primary Examiner—Paul B. Prebilic
Attorney, Agent, or Firm—Arnall Golden & Gregory, LLP

[57] ABSTRACT

Methods for forming implantable composite keratoprostheses are provided. The methods provide keratoprostheses designed to provide a suitable substrate for corneal epithelial cell growth while maintaining the desirable characteristics of hydrogels, i.e., clarity, flexibility and the ability to allow diffusive flow of nutrients. In a preferred embodiment the method includes placing corneal tissue in a mold having a corneal implant shape and crosslinking a polymeric solution to chemically bond a biocompatible hydrogel having a thickness between approximately 50 and 100 microns to the corneal tissue to form the keratoprosthesis. Upon implantation, the corneal tissue abuts epithelial cells surrounding the keratoprosthesis. In another preferred embodiment, a polymer solution is placed between the corneal tissue and a pre-formed hydrogel and then polymerized so that the polymer solution couples to both the hydrogel and the corneal tissue.

9 Claims, 1 Drawing Sheet

OTHER PUBLICATIONS

King, J.K., "Deciphering the Rules of Protein Folding", *Chem. Engin. News*, 67(10):32–54 (1989).

Kirkham, S.M., et al., "The Keratoprosthesis: Improved Biocompatibility Through Design and Surface Modification", Abstracts—17th Cornea Research Conference, Boston (1991).

Komai, Y., et al., "The Three–Dimensional Organization of the Collagen Fibrils in the Human Cornea and Sclera", *Invest. Ophthal. Vis. Sci.*, 32:2244–2258 (1991).

Maroudas, N.G., "Chemical and Mechanical Requirements for Fibroblast Adhesion", *Nature*, 224:253 (1973).

Maurice. D., "The Cornea and Sclera in the Eye", Academic Press, Florida. Davson, H., editor, 1B:1–158 (1984).

McCarey, B.E., et al., "Refractive Keratoplasty with Hydrogel Lenticular Implants", *Invest. Ophthal. Vis. Sci.*, 21:107–115 (1981).

Merrill E.W., et al., "Polyethylene Oxide as a Biomaterial", *Amer. Soc. for Art Int. Organs*, 6(2):60–64 (1993).

Merrill E.W., et al., "Nonadsorptive Hydrogels for Blood Contact", Progress in Artificial Organs, ISAO Press, Cleveland, 909–912 (1986).

Oliver, et al., "The Fate of Cutaneously of Subcutaneously Implanted Trypsin Purified Dermal Collagen in the Pig", *Brit. J. Exp. Path.*, 53(5):540–549 (1872).

Petit, D.K., et al, "Quantitation of Rabbit Corneal Epithelial Cell Outgrowth on Polymeric Substrates In Vitro", *Invest, Ophthal. Vis. Sci.*, 31(11);2269–2277 (1990).

Pietrucha, K., et al., "Radiation Crosslinking of Poly(butyl acrylate) During Polymerization and Grafted Copolymerization with Cr(III) Crosslinked Collagen", *Radiation Physics Chem.*, 28(9):373–376 (1986).

Pietrucha, K., et al., "Some Reactions of OH Radicals with Collagen and Tyrosine in Solutions", *Rad. Physics Chem.*, 36(2):155–160 (1990).

Rao, et al., "Grafting of Vinyl Monomers onto Modified Collagen by Ceric Ion –Studies on the Grafting Sites", *Leather Sci.*, 16, (1969).

Rao, K.P., et al., "Collagen Graft Copolymers and Their Biomedical Applications in Collagen", Nimni, M.E., ed., CRC press, Boca Raton, Florida, 3:63–85 (1988).

Refoio, M.F., "Artificial Membranes for Corneal Surgery", *J. Biomed. Mater. Res.*, 3:333–337 (1969).

Rioslahti, E. et al., "Arg–Gly–Asp: A Versatile Cell Recognition Signal", *Cell*, 44:517–518 (1986).

Salthouse, T.N., et al., "Some Cellular Effects Related to Implant Shape and Surface in Biomaterials in Reconstructive Surgery", Rubin, ed. (St Louis, Mosby), 40–45 (1983).

Shultz, A.R., "Radiation and Crosslinking by Radiation", Fettes EM (ed). Chemical Reactions of Polymers. Interscience. New York (1964).

Silverstein, et al., "Spectrometric Identification of Organic Compound", 4th Ed, John Wiley and Sons, Inc. New York (1981).

Sipehia R. et al., "Towards an Artificial Cornes", *Biomat., Art Cell, Art Organs*, 18(5):643–655 (1990).

Stafford, J.W., "The Irradiation Induced Reactions of Aqueous Polyethylene Oxide Solution, I, Theory of Gelation", *Die Makromolekulare Chemie*, 134:57–69 (1970).

Sugimoto, Y, "Effect on the Adhesion and Locomotion of Mouse Fibroblasts by their Interacting with Differntly Charged Substrates", *Exp. Cell Res.*, 135:39 (1981).

Thompson, K.P., "Current Status of Synthetic Epikeratoplasty", *Refractive Corneal Surg.*, 7:240–248 (1991).

Thompson, et al., "Synthetic Collagen IV lenticules as a biomaterial for epikeratoplasty", *ARVO Absts. Invest. Ophthal. Vis. Sci.*, 31(suppl):301 (1990).

Thompson, K.P., et al., "Synthetic Collagen IV lenticules as a biomaterial for epikeratoplasty", ARVO Abstracts, *Invest. Ophthalmol. Vis. Sci.*, 31(suppl):301 (1990).

Trinkhaus–Randall, V. et al., "The Development of a Biopolymeric Keratoprosthetic Material", *Invest. Ophthal. Vis. Sci.*, 29(3):393–400 (1988).

Udenfriend. S., et al., "Fluorescamine: A Reagent for Assay of Amino Acids, Peptides, Proteins, and Primary Amines", *Science*, vol. 178 (1972).

Vandeberg. J.T. (editor), "An Infrared Spectroscopy Atlas for the Coating Industry", Federation of the Society for Coating Technologies, Philadelphia, PA, (1980).

Weetal, H.H. (editor), "Immobilizing Enzymes, Antigen, Antibodies and Peptides: Preparation and Characterization", Marcel Dekker Inc. New York (1975).

Wilson, J.E., "Radiation Chemistry of Monomers, Polymers, and Plastic", Marcel Dekker, Inc., New York, NY (1974).

Yannas, IV, "Collagen and Gelatin in the Solid State", *J. Macromolecular Sci.–Revs. Macromol. Chem.*, C7(1):49–104 (1972).

Zurawski, C.A., et al., "Glucose Consumption in Cultured Corneal Cells", *Current Eye Research.* 9(4):349–355 (1989).

Perez, et al. "Bilayer Composite Hydrogels for Corneal Prostheses" Mat. Res. Soc. Symp. Proc. vol. 252, pp. 375385 (May 1992).

METHODS FOR MAKING COMPOSITE HYDROGELS FOR CORNEAL PROSTHESES

This is a continuation-in-part of copending U.S. Ser. No. 08/384,378 filed on Feb. 3, 1995, which is a continuation of U.S. Ser. No. 08/014,812 filed on Feb. 8, 1993, now abandoned, and claims priority to PCT/US94/01419 filed Feb. 9, 1994.

BACKGROUND OF THE INVENTION

The present invention is generally in the field of ocular materials and in particular is an improved hydrogel material for engineering of corneal surfaces.

The major anatomic divisions of the eye are the sclera, uveal tract, retina, vitreous, lens, anterior chamber, and the cornea. The clear cornea and gray-white opaque sclera are fused together and completely enclose the other portions of the eye. Under the influence of intraocular pressure, the cornea and sclera form a semi-rigid spherical organ.

The cornea occupies the anterior pole of what is referred to as the globe. In adults, the cornea measures 12 mm in the horizontal meridian and 11 mm in the vertical meridian. The central one-third of the cornea is nearly spherical and measures 4 mm in diameter. The cornea is thinner (0.5 mm) in the center than in the periphery (1.0 mm). Histologically, the cornea is composed of five layers: epithelium, Bowman's membrane, stroma, Descemet's membrane, and endothelium. The most metabolically active layers are the limiting layers, as described by Zurawski C A, McCarey B E, and Schmidt: Glucose Consumption in Cultured Corneal Cells. (1989) Current Eye Research 9(4), 349–355: endothelium and epithelium, which are primarily cellular. The epithelium serves to maintain the tear film and provide an anatomic barrier to infectious agents. In contrast to the limiting layers, the stroma is only 3–5% cellular, consisting mainly of collagen type I. As a result, 70% of dry weight of the cornea is collagen type I, with the balance being glycosaminoglycans and cellular elements. The cornea is 77% water under normal physiologic conditions. The stroma serves to mechanically maintain the geometry of the cornea, as described by Maurice D: The Cornea and Sclera. in The Eye, Vol 1B, Davson H, editor. Florida, 1984, Academic Press, pp 1158.

Irreversible loss of corneal tissue clarity is treated by replacement of the patient's cornea, usually with a donor cornea, as reviewed by Brightbill F S, Corneal Surgery: Theory, Tissue, and Technique. The C. V. Mosby Company St Louis, Mo. (1986). In spite of the success of corneal transplants, there is a still a need for a viable prosthetic alternative. Keratoprostheses are generally indicated in cases of chemical burns, ocular pemphigoid (severe dry eyes), heavily vascularized corneas, and in cases of multiple graft failures. A viable prosthetic alternative to corneal transplants is also needed for treatment of severely intractable cornea cases as well as for cases in underdeveloped countries where human corneal tissue is unavailable due to poor donor supply and storage conditions. In addition, the appearance of AIDS and other tissue-borne diseases has caused increased scrutiny and mistrust of donor tissue even in developed countries.

When considering the synthetic replacement of the cornea, two major functional issues must be addressed. The first issue is the optical function and the second is the anatomic barrier function of the cornea. Use of synthetic materials in corneal surgery has existed, at least theoretically, since 1771 when Pellier de Quengsy conceived of implanting transparent material in the scarred cornea. In the late 1800's, glass buttons were implanted into the cornea to increase the clarity of scarred corneas. Modern devices have been designed as optically clear poly (methyl methacrylate) cylinders that penetrate the cornea and are anchored by a collar, as reported by Cardona H: Keratoprosthesis. Ophthalmology (1976) PP 284–299. These prostheses are short lived due to the progressive necrosis and stromal "melting" of the cornea close to the cylinder. The impermeability and rigidity of these devices are believed to eventually cause the failure of the device. Since there is no complete barrier (epithelium) covering the implant, the edges of the implant also serve as a site for infection.

The complete replacement of the cornea including one or both of the limiting layers (epithelium or endothelium) is still addressed with materials such as poly (methyl methacrylate) or silicone membranes. These currently used keratoprostheses have relatively short lifetimes of between a few weeks and a few months as a result of no continuous epithelial boundary, tissue death around the implant (sterile necrosis), secondary infection (endophthalmitis), and peri-implant membrane formation.

Upon the re-evaluation of the concept of a prosthetic cornea, the issue of biological activity, i.e., cell and tissue response, of synthetic surfaces became a consideration. In either therapeutic or refractive corneal surgery, the growth of epithelium over the implant is important. Normally, the epithelium is a labile cellular population which will grow back over a denuded area of the cornea. Thus, a synthetic corneal surface must provide an environment that is conducive to epithelial cell growth.

Analysis of the surface chemistry of synthetic material surfaces conducive to epithelialization yields several basic conclusions, reported by Baier R E et al: Surface Properties Determine Bioadhesive Outcomes: Methods and Results. 1984 *J. Biomed. Mater. Res.* 18:337; Sugimoto Y: Effect on the Adhesion and Locomotion of Mouse Fibroblasts by their Interacting with Differently Charged Substrates. 1981 *Exp. Cell Res.*, 135:39; Maroudas N G: Chemical and Mechanical Requirements for Fibroblast Adhesion. 1973 *Nature* 244:253; Salthouse T N and Matlaga: Some Cellular Effects Related to Implant Shape and Surface: in *Biomaterials in Reconstructive Surgery.* 1983 Rubin, ed. (St Louis, Mosby); pp 40–45; Curtis A S G et al: Substrate Hydroxylation and Cell Adhesion. 1986 *J. Cell Sci.* 86:9; Petit D K et al: Quantitation of Rabbit Corneal Epithelial Cell Outgrowth on Polymeric Substrates In Vitro. 1990 *Invest. Ophthal. Vis. Sci.* 31(11) 2269–2277. Factors such as negative charge, intermediate wetabilities, moderate hydroxylation, and low polymer chain rigidity are believed to be conducive to epithelialization. These surface factors include wetability: 45°–75°; composition: high [OH], low [COOH]; chain rigidity: low Mobility; Charge Density: Negative $(2000/10(-11)$ cm$)^2$.

In spite of identification of these factors, these investigators could not rule out the contribution of surface protein adsorption which aided in the adherence of cells. Protein or peptide attachment to surfaces is an attractive method of surface modification. Proteins which are involved in cell-substratum interaction have been shown to enhance the adherence of cells to synthetic surfaces, as reviewed by Rioslahti E, Pierschbacher M D; Arg-Gly-Asp: A Versatile Cell Recognition Signal. 1986 *Cell* 44, 517–518. Efforts to specifically utilize the these proteins to enhance the adherence of corneal epithelial cells has been performed with PVA copolymer hydrogels, Trinkhaus-Randall V et al: The Development of a Biopolymeric Keratoprosthetic Material. 1988

*Invest. Ophthal. Vis. Sci.* 29(3), 393–400. Although the initial cell-hydrogel adherence is enhanced, prolonged attachment is not maintained. This finding is probably because the methodology of coating surfaces with proteins is based fundamentally on adsorption of these proteins.

It was not until recently, as reviewed by Trinkhaus-Randall V et al: The Development of a Biopolymeric Keratoprosthetic Material. 1988 *Invest. Ophthal. Vis. Sci.* 29(3), 393–400, that hydrogels had been evaluated as useful materials for a prosthetic device that would penetrate either the epithelial or endothelial side of the cornea. Hydrogels were originally conceived only as intrastromal implants. The clinical application of these intra-corneal hydrogels was to affect the shape of the cornea, as reported by McCarey B E, Andrew D M: Refractive Keratoplasty with Hydrogel Lenticular Implants. 1981. *Invest. Ophthal. Vis. Sci.* 21, 107–115. Initially three different hydrogel materials were used in corneal surgery: poly(2-hydroxyethyl methacrylate) PHEMA, poly(glycerol methacrylate) PGMA, and polyelectrolyte materials, described by Refojo M F: Artificial Membranes for Corneal Surgery. 1969 *J. Biomed. Mater. Res.* 3, 333–337. The desired characteristics of these materials were essentially their bulk characteristics such as: solute permeabilities, chemical and mechanical stability, and optical clarity. The only biological characteristics these materials had to possess is that they be non-inflammatory.

Another approach to this problem attempts to synthesize a material whose intrinsic surface is one conducive to epithelial cell growth. The synthesis of these materials utilizes crosslinking methods to form hydrogels from the collagen types (I, described by Geggel H S, Friend J, and Throft R A: Collagen Gels for Ocular Surface. 1985 *Reports Invest. Ophthal. Vis. Sci.* 26: 901–905, and IV, described by Thompson et al. Synthetic Collagen IV lenticules as a biomaterial for epikeratoplasty. 1990 ARVO Absts. *Invest. Ophthal. Vis. Sci.* 31(suppl), 301. Unfortunately, materials like these have been found to be susceptible to proteolysis in vivo. As reported by other investigators, Rao K P and Joseph K T: Collagen Graft Copolymers and Their Biomedical Applications in Collagen, Vol 3, Nimni, M. E., ed. (CRC press, Boca Raton Fla. 1988) pp 63–85, and Franzblau C et al: Cell Growth on Collagen-HEMA Hydrogels. id. pp 191–208, have synthesized collagen-HEMA copolymers to grow epithelial cells. These materials were also found to be susceptible to proteolysis and were brittle.

To summarize, the current modalities using proteins or peptides as materials for hydrogel-fabrication or hydrogel-surface-modification are confounded by factors such as proteolytic digestion, poor protein adherence to the synthetic surface, and brittleness or fragility. However, even considering these factors, utilizing cell-adhesion proteins immobilized on a synthetic surface is attractive since these proteins are ultimately involved in in vivo epithelialization.

Refractive errors are presently corrected with the use of eyeglasses or contact lenses. Another major application of synthetics in corneal surgery is the rising interest in refractive surgery, as reviewed by Thompson K P: Current Status of Synthetic Epikeratoplasty. Refractive and Corneal Surgery 7:240–248. In theory, a refractive prosthesis could affect the curvature of the corneal surface and influence the cornea's ability to focus an image on the retina thereby circumventing the need for glasses.

Implanting material onto the cornea is receiving much attention as a means of correcting refractive errors. These superficial corneal augmentations have been termed epikeratophakic grafts. Originally, epikeratophakic grafts were made from donor corneal tissue. These were not optimal, however, because of difficulty in manufacture, requiring two to three weeks post-operatively to regain clarity, and susceptibility to normal tissue remodeling processes. Synthetic epikeratophakic grafts offer ease in manufacturing and stability in clarity and geometric form. However, in the effort to develop usable synthetic epikeratophakic grafts, investigators have identified difficulties with the synthetic materials as a result of the lack of normal regeneration of the epithelial cell layer on these materials. As a result, the development of a synthetic graft with a suitable surface for regeneration of an epithelial cell layer, which maintains the desired optical and structural properties, is required to make these devices clinically useful.

Collagen coating of conventional hard poly (methylmethacrylate) (PMMA) corneal prostheses, as described by Kirkham S M, Dangel M F: The Keratoprosthesis: Improved Biocompatibility Through Design and Surface Modification. Abstracts—17th Cornea Research Conference, Boston (1991), increases the attachment of these devices to tissue and decreases the inflammatory responses. Still, the lifetime of these conventional, impermeable PMMA devices is short (15 months) and they are never fully epithelialized.

Hydrogel materials have received much attention in relation to their applicability as prosthetic corneal devices, as reported by Trinkhaus-Randall V et al: The Development of a Biopolymeric Keratoprosthetic Material. *Invest. Ophthal. Vis. Sci.* Vol. 29, No. 3 (1988) pp. 393–400; Sipehia R, et al. Towards an Artificial Cornea. *Biomat., Art Cell, Art Organs;* 18(5) pp. 643–655 (1990); and Thompson K P: Current Status of Synthetic Epikeratoplasty. *Refractive Corneal Surg.* Vol. 7 (1991) pp. 240–248, because of the properties of hydrogels, including clarity, flexibility, and ability to allow diffusive flow of nutrients. Anatomically, a penetrating corneal prosthesis must be fully enclosed in the cornea with a contiguous epithelium; i.e., contiguous epithelium must develop between the implant and host via colonization of the implant surface by epithelial cells which migrate from the host cornea. Ideally, a hydrogel material must be constructed possessing a surface environment conducive to corneal epithelial cell growth in addition to maintaining other desirable characteristics of hydrogels. This has not yet been achieved.

It is therefore an object of the present invention to provide keratoprostheses that have longer lifetimes, and result in less tissue death, secondary infection and peri-implant membrane formation following implantation, than currently available keratoprostheses.

It is a further object of the present invention to provide a method for making and using a material with desirable optical properties, including clarity, providing an optimal epithelial cell substrate, tissue-like flexibility, and permeability to solutes, which is compatible in living systems and enzymatically stable, for use as keratoprostheses.

SUMMARY OF THE INVENTION

A two-layer composite material composed of a thin-layer of corneal tissue or collagen and a hydrogel, preferably formed of an electron-beam crosslinkable polymer such as a synthetic polyethylene oxide (PEO) hydrogel, is described. The material is designed to provide a suitable substrate for corneal epithelial cell growth while mainlining the desirable characteristics of hydrogels, i.e., clarity, flexibility and ability to allow diffusive flow of nutrients.

In the preferred embodiment shown in the examples, the gels are synthesized via electron irradiation induced crosslinking of an aqueous solution of PEO onto a thin layer of collagenous tissue substrate. In a second embodiment, the collagenous tissue substrate, or stromal layer, is glued to a preformed hydrogel by polymerization of a liquid polymer solution, for example a polyethylene oxide solution that is polymerized by electron beam irradiation. Light microscopic studies indicate that the interface between the corneal tissue and PEO gel appears well adherent with no gaps in the interface. SEM studies of the material surface show an architecture similar to that of normal corneal tissue. Surface analytical techniques were used to identify amino-acids covalently bound to the gel at the gel/collagen interface after the proteinaceous material was removed. ESCA survey scans identified the presence of nitrogen on exposed gel/collagen interfaces and amino acid labelling confirmed the presence of amino acids. ATR-IR studies identified increased absorption for the gel collagen interfaces at 1640 $cm^{-1}$ and 1540 $cm^{-1}$ indicative of bound amino acids. In vivo studies are being used to confirm biocompatibility, optical properties, and mechanical stability over extended periods.

DETAILED DESCRIPTION OF THE INVENTION

A hydrogel composite whose ultimate use will be for the construction of an artificial cornea or epikeratoprostheses has been synthesized. The design rationale is to construct a material possessing a surface environment conducive to epithelial cell growth in addition to possessing the proper optical, diffusive, and mechanical characteristics of the cornea. In the preferred embodiment, electron-irradiation-induced (EII) crosslinking is used to synthesize a hydrogel network and simultaneously attach the polymeric network to a collagenous substrate.

Described herein is a material, and methods of use thereof as a synthetic lenticule or epikeratophakic graft, synthesized of a composite material formed of a synthetic hydrogel covalently attached to a thin collagen matrix. There are essentially two embodiments, the first where the hydrogel is covalently attached directly to the collagen (or stromal) matrix and the second where there is an intermediate material which is used to adhere the collagen matrix to the hydrogel. In the presently most preferred embodiments, polyethylene oxide (PEO) or hydroxyethylmethacrylate (HEMA) and excised corneal stromal tissue are used to synthesize the hydrogel and matrix surface.

Selection and Preparation of the Hydrogel

As used herein, a hydrogel is a water swollen polymer, between two weight percent and 60 weight percent per volume of gel. Hydrogels are typically 80 to 90% water, having indices of refraction close 1.3, which is similar to that of water and, therefore the cornea. Mechanically, the hydrogels should be able to support a breaking tensile stress of between 40,000 and 60,000 dynes/$cm^2$. This is a relatively weak force. The polymer should be completely transparent to visible light and not absorb in the range of 300 nm to 850 nm. Chemically, the hydrogels should remain stable and not degrade in vivo. Small amounts of degradation product can cause an inflammatory response.

All hydrogel materials implanted into the center of the cornea have proven to be perfectly compatible and yield no deleterious effects, presumably in part because the cornea is not a vascularized organ and is therefore privileged, or isolated, from the immune system. In other parts of the body that are vascularized, reactive functional groups on the surface of hydrogels, including amines, carboxyls, and hydroxyls, have been associated with inflammation. As described below, combining these materials with corneal stroma or collagen appears to make all of the hydrogels biocompatible within the corneal environment.

A number of polymers can be used to form the hydrogel, including hydroxyethylmethacrylate, polyethylene oxide, polyvinyl alcohol, polydioxolane, poly(acrylic acid), poly (acrylamide), and poly(N-vinyl pyrilidone). These polymers can be crosslinked by electron beams. These materials are commercially available from Polysciences, Sigma Chemical Co., and Aldrich Chemical.

In the preferred embodiment, the hydrogel is formed of crosslinked polyethylene oxide or hydroxyethylmethacrylate. Crosslinked PEO has previously been used in the synthesis of hydrogel materials for corneal implantation, as reported by Peiffer R L, Werblin T P, Fryczkowski A W: Pathology of Corneal Hydrogel Alloplastic Implants. Ophthalmology Aug 1985, 92(9) p. 1294–1304. These materials have shown negligible tissue reaction and do not adsorb proteins, as reported by Merrill E W, Salzman E W: Polyethylene Oxide as a Biomaterial. Amer. Soc. for Art Int. Organs, Vol. 6, No. 2 April/June (1983) p. 60–64; Merrill E W, et al.: Nonadsorptive Hydrogels for Blood Contact. Progress in Artificial Organs, ISAO Press, Cleveland (1986) pp. 909–912.

The polymer solutions to be crosslinked range from 2 to 15 weight per volume. The preferred thickness in combination with corneal tissue or collagen is in the range of between 50 and 100 microns.

In a preferred embodiment, electron-irradiation-induced (EII) crosslinking is used to crosslink a hydrogel network onto a collagenous matrix substrate, which serves as a substrate for cell growth. EII crosslinking is described by Dole M: The Radiation Chemistry of Macromolecules. Academic Press, new York (1972) and Shultz, A R: Radiation and Crosslinking by Radiation, in Fettes E M (ed), Chemical Reactions of Polymers. Interscience, New York 1964), the teachings of which are incorporated herein, and described in more detail in the examples below. Water is the only solvent used for electron beam crosslinking. An advantage of this method is that it can be used to polymerize and sterilize at the same time.

Other methods can be used to synthesize hydrogels. Either covalent chemical or physical bonds can be used to adhere the hydrogel to the corneal tissue or collagen. For example, endlinking of polymers with functionalized ends can be used. A hydrogel can also be formed by polymerizing monomer in the presence of crosslinking agents, such as by polymerizing acrylamide and bis acrylamide in the presence of a free radical initiator like ammonium persulfate. Endlinking and polymerizing a network is performed in a non-polar solvent such as hexane.

Preparation of the Collagen Matrix

The hydrogel is prepared in a mold shaped to provide an implant with the appropriate surface for placement in the eye and replacement of optical and physiological function, i.e., which maintains the desired geometry of the lens. The mold will typically contain a layer of corneal stroma or collagen which the hydrogel is bonded to. The hydrogel is ultimately placed on the inside of the eye, so that the epithelial cells adjacent to the implant abut the stroma or collagen and can grow over the surface of the implant. As noted above, the hydrogel will preferably be in a layer of between 50 and 100 microns. The corneal tissue or collagen layer will preferably be in a layer of between 10 and 50 microns.

A thin layer of between approximately 10 $\mu$m and 50 microns of corneal tissue is grafted to the surface of a hydrogel to form a suitable surface for cell growth and to impart added mechanical stability to the device. The tissue is preferably obtained fresh, frozen to −20° C. cut on a microtome. After the tissue is placed in the mold, the tissue is lyophilized.

Corneal tissue can be obtained from the same or different species since xenogeneic tissue exchange has been shown to form viable corneal transplants. Human corneal tissue is obtained from commercial eye banks. Rabbit eyes have also been used as a source of tissue, with up to thirty films being obtained from one rabbit cornea. Bovine eyes can also be used as donor material. As noted above, the material is preferably lyophilized, which further decreases the likelihood of a reaction against the material.

The bulk of the cornea is collagen I (70% of dry weight) with the balance being glycosaminoglycans and cellular elements, as reviewed by Maurice D: The Cornea and Sclera. in the Eye, Vol. 1B, Davson H, editor. Florida, 1984, Academic Press, pp. 1–158. Collagen type I has been proven to be a suitable substrate for epithelial growth in a variety of circumstances. Collagen type I also contains peptide regions known to be involved in cell-substrate adhesion. Collagen in modified forms is a good substrate for growth of many cell types, as reported by Geggel H S, Friend J, and Throft R A: Collagen Gels for Ocular Surface. *Rep. Invest. Ophthal. Vis. Sci.;* 26: 901–905 (1985); Thompson K P, Hanna K D, and Gravagna P. et al. Synthetic Collagen IV lenticules as a biomaterial for epikeratoplasty. ARVO Abstracts. *Invest. Ophthalmol. Vis. Sci.* 1990; 31 (suppl):301. Modified forms of collagen type I are commercially available as a substrate for cellular growth. In addition to its ability to sustain cellular growth, fibrillar collagen I is not susceptible to non-specific proteolytic enzymes, Oliver et al. 1872 The Fate of Cutaneously or Subcutaneously Implanted Trypsin Purified Dermal Collagen in the Pig. *Brit. J. Exp. Path.* 53(5), 540–549. Lastly, fibrillar corneal collagen oriented in its normal tissue architecture can provide increased tensile strength to the surface of the implant.

In an effort to utilize corneal collagen to modify the surface of a hydrogel, the first concern is the conservation of tissue architecture of collagen. In some cases the bonding is only by passive adsorption. This is a simpler approach than by chemical bonding and does not attempt to preserve the higher organizational structure of collagen in vivo. Collagen in corneal tissue is organized into a complex structure of fibrils oriented in parallel planes. The collagen in this tissue architecture is not easily manipulated in processing techniques unless it is solubilized, yet its soluble form no longer has the architecture it has in connective tissue.

Using the techniques described herein, the mechanical stability and substrate properties of the native structure, Azar D T, et al. "Reassembly of the Corneal Epithelial Adhesion Structures Following Human Epikeratoplasty", Archives of Ophthalmology Vol. 109, Sept. 1991 pp. 1279–1284, is exploited for better maintenance of a contiguous epithelial cell layer. This is in contrast to the prior art methods of attaching proteins onto hydrogels which bind single protein molecules or small molecular aggregates onto surface sites, reported by Weetal H H (editor), Immobilizing Enzymes, Antigen, Antibodies and Peptides: Preparation and Characterization. Marcel Dekker Inc. New York (1975), which disrupts the higher organizational structure of collagen exhibited in vivo. Corneal collagen is not easily manipulated in processing techniques unless it is solubilized, yet its soluble form no longer has the architecture it has in corneal tissue, King J K: Deciphering the Rules of Protein Folding. *Chem. Engin. News;* 67(10) pp. 32–54 (1989). An advantage of the EII crosslinking procedure is that it does not require the solubilization of the tissue, and thus the native architecture is preserved in the final device.

In addition to corneal collagen, films of less than 20 microns thick cross-linked collagen type I have been used to develop cross-linking strategies and analytical techniques.

Formation of Lenticules and Epikeratophakic Grafts

Attaching fibrillar collagen onto a hydrogel to modify the surface is dependent upon achieving a satisfactory adherence between collagen and the hydrogel. The hydrogel can be bound to the collagen matrix by mechanical or chemical coupling. Covalently bonding collagen directly or indirectly onto a synthetic hydrogel network by crosslinking provides optimal adhesion. To address both the conservation of fibrillar corneal collagen form and the interface bonding between materials, electron-irradiation-induced (EII) crosslinking is used to adhere a layer of corneal collagen to polymer molecules of a hydrogel network. In one embodiment, the electron beam simultaneously synthesizes and crosslinks the hydrogel onto the insoluble collagenous substrate. In a second embodiment, the electron beam is used to polymerize a polymer layer between the collagen matrix and the hydrogel which thereby covalently crosslinks the hydrogel to the collagen matrix. A number of polymeric materials can be used to attach the hydrogel to the collagen matrix, including any of the materials described above with reference to formation of the hydrogel itself. These materials can be the same as or different from the material forming the hydrogel.

Electron-beam irradiation has been used extensively to crosslink polymers onto hydrogels and also to attach polymers onto surfaces, as reported by, for example, Wilson J E: Radiation Chemistry of Monomers, Polymers, and Plastic. Marcel Dekker, Inc., New York, N.Y. (1974). This method is confined to a surface attachment of polymer molecules since there is no diffusion into the collagen fibers. EII crosslinking has previously been used to form strong attachment of collagen onto a surface, as disclosed by U.S. Pat. No. 3,955,012 to Okamura and Hino. Microfibrillar collagen aggregates were adhered with EII crosslinking to silicone membranes and found to be adherent in peel tests even after 10 days of washing. In contrast, the use of monomer molecules allow monomer diffusion into the collagen and affects the physical and biological properties of the material. Using a high dose rate, between 0.5 and 100 Mrads/sec, for example, for a few seconds to generate a total dose of 2 Mrads, hydrogels can be synthesized which are covalently bound to fibrillar collagen. This type of crosslinking is achieved by use of a Vandergraf generator, which generates up to a dose of 0.5 Mrads/second. The higher the dosage, the greater the amount of crosslinking.

However, the dosage and extent of crosslinking must be limited to avoid damage to the underlying corneal tissue or collagen substrate, which causes, for example, the tissue to become opaque.

This crosslinking mechanism is based upon chemical activation of polymer molecules that result in the formation of polymer-polymer crosslinks to form a hydrogel and polymer-collagen, as reported by Pietrucha K, Kroh J: Radiation Crosslinking of Poly(butyl acrylate) During Polymerization and Grafted Copolymerization with Cr(III) Crosslinked Collagen. 1986 *Radiation Physics Chem.* 28(9) ,373–376; and Rao et al. Grafting of Vinyl Monomers onto Modified Collagen by Ceric Ion-Studies on the Grafting Sites. 1969 *Leather Sci.* 16, crosslinks to unite the collagen and hydrogel.

The crosslinking process initiated by electron irradiation creates covalent attachment between the substrate collagen and the forming synthetic polymer network. However, less than 1% of electrons directly affect the polymer chains themselves, as reported by Stafford J W: The Irradiation Induced Reactions of Aqueous Polyethylene Oxide Solution, I. Theory of Gelation. 1970 *Die Makromolekulare Chemie* 134, 57–69. Hydroxyl radicals formed from the electron induced lysis of water attack hydrogens on polymers and collagen. These attacks leave radicals on the macromolecules which can recombine to form covalent crosslinks. The adherence or bonding between the insoluble collagen substrate and the hydrogel network arise from collagen amino acids crosslinked to synthetic polymer, as expected based on Pietrucha K, Lobis M: Some Reactions of OH Radicals with Collagen and Tyrosine in Aqueous Solutions. 1990 Rad. Physics Chem. 36(2), 155–160.

Solution characteristics and irradiation conditions affect the degree of polymer-collagen crosslinking. These factors can be theoretically considered by examining the major reactions, the radical generation reactions and the crosslinking reactions. The radiolysis of water is a fast reaction which creates a concentration of hydroxyl radicals, [$OH^-$], that are consumed as fast as they are created. These hydroxyl radicals, $OH^-$, participate in the creation of macroradicals on polymers in solution. Scission that takes place is not considered since it is first order whereas recombination of macroradicals is second order (bimolecular). Factors which increase the concentration of macroradical should also increase the amount of crosslinking. Dose rate (Mrad/sec) directly affects the concentration of hydroxyl radicals. Polymer concentration affects the concentration of hydroxyl radicals. Polymer concentration affects the amount of collagen-polymer crosslinking by the increased availability of polymer radicals. Since the amount of collagen is fixed in a given area, only an increase in dose rate affects the concentration of collagen radicals. Since the amount of collagen is fixed in a given area, only an increase in dose rate affects the concentration of collagen radicals. The relative proportion of collagen-polymer to polymer-polymer crosslinks is governed by the ratio of rate constants $k_{p,c}$ and $k_{p,p}$ and the polymer concentration. Collagen concentration is essentially fixed per a certain area.

Formation of and Implantation of Composites

These considerations aside, the collagen or corneal tissue substrate is placed in a mold of the appropriate desired shape. For example, corneal tissue layer substrates are prepared by slicing tissue using a cryostat or microtome to a thickness between 10 and 80 microns, at a plane tangential to the surface of the cornea. The layers are placed in a pre-cooled (–20° C.) glass mold in the shape of the final product. An aliquot of the polymer solution is placed onto the substrate, then exposed to an electron beam in a dose sufficient to crosslink the solution into a gel so that its final dimensions will be stable. Although the mold determines the basic shape and dimensions of the final product, this is then shaped in the same manner as other types of keratoprostheses or contact lens, trimming off material as necessary to achieve the desired curve in the cornea.

The implant is then placed in a patient's eye using standard techniques for implantation of keratoprosthesis. For example, the eye is topically anesthetized with 4% proparacaine HCl. After a few minutes, the cornea is locally anesthetized with 4% proparacaine by subconjunctival injections, and the eye is immobilized with a lid speculum, which simultaneously keeps the eyelids open and the eye fixed, as necessary. A sterile drape is placed around the eye. Absolute ethanol is applied to the central five mm of the cornea to remove the central epithelial layer. The epithelium is further debrided from the central cornea using the blunt side of a scalpel blade. The debrided surface is then irrigated using sterile balanced salt solution (BSS) to remove any other epithelial debris. Using a five mm trephine, a superficial circular incision is made in the central cornea to a depth of 0.1 mm. A lamellar keratotectomy is performed on the central core of the cornea. A circumferential incision is then made using a rounded scalpel blade. The implant is tucked into the annular incision that has been created. The wound edges are sealed either with sutures, or, more preferably, by air-drying for three to five minutes. A pressure patch is then applied to keep the eyelid from moving over the eye surface for at least two days, to allow healing and epithelialization of the implant surface.

The present invention will be further understood by reference to the following non-limiting examples.

EXAMPLE 1

Synthesis and Characterization of PEO Hydrogels Prepared by EII Crosslinking of Polyethylene Oxide (PEO) to a Substrate of Fibrillar Collagen Light microscopy and scanning electron microscopy were used to visualize the gel/collagen interface. The materials were characterized by several chemical and spectroscopic techniques to elucidate the nature of the bonding of PEO to a substrate of collagen. Bulk proteinaceous material was removed with oxalic acid hydrolysis so the gel/collagen interface could be exposed. Electron spectroscopy for chemical analysis (ESCA) was used to determine the presence of nitrogen from amino acids on the surface. Fluorescamine amino-acid labelling was used to confirm that the nitrogen present was in amino-acid form. Attenuated Total Reflection Infrared (ATR-IR) spectroscopy was used to determine IR spectral changes indicative of bound amino acids.

MATERIALS AND METHODS

Synthesis of Composite Gels

Collagenous substrates were either dried films of bovine collagen I (100 μm) or bovine corneal tissue (10 μm). Collagen films were made by air-drying a 10 mg/ml solution of microfibrillar collagen (Avitene, MedChem Products, Woburn, Mass.) placed in a 25 mm polypropylene dish. Later the films were vacuum dried for 24 hours. Sheets of corneal tissue were cut from the anterior half of the adult bovine cornea on a cryostat (Tissue Tek II) set at –22° C. The collagen substrates, from either method, were supported on glass coverslips during electron beam irradiation. An aqueous solution of 5% PEO (MW=100K) is introduced into a 550 μl disc shaped vessel where the samples and coverslip supports are placed. Samples are irradiated from 7.5 to 10 Mrads at dose rates of 0.5 Mrad/sec. Samples of corneal tissue grafted onto PEO gels were examined under light and scanning electron microscopy. Collagen films grafted onto PEO gels were examined with analytical techniques such as ESCA, amino-acid labelling, and surface infrared spectroscopy. For characterization of the PEO gel/collagen interface, the collagen grafted onto PEO was removed through hydrolysis, using the method of Pietrucha K, Kroh J: Radiation Crosslinking of Poly(butyl acrylate) During Polymerization and Grafted Copolymerization with Cr(III) Crosslinked Collagen. Radiation Physics Chem. 28(9) pp. 373–376 (1986), with 10% oxalic acid for 150 hours to leave only amino acids covalently bound to the gel surface.

Light and Scanning Electron Microscopy

PEO hydrogels grafted onto corneal tissue were prepared into 6 $\mu$m sections and stained with hematoxylin and eosin for light microscopy. The samples prepared for SEM were fixed in glutaraldehyde and stained with $OsO_4$. The samples were dried in a critical point dryer (AUTOSAMDRI model 814) and visualized in a dual stage scanning electron microscope (model ISI-DS130).

Fluorescamine Labeling

The gel networks with collagen hydrolytically removed were buffered with 2 volumes of 0.2M sodium borate buffer. One volume of fluorescamine (15 mg/100 ml acetone) was added to the mixture, giving an approximately 20-fold excess versus protein, if 0.6 $\mu g/cm^2$ of protein binds to the hydrogel surface, as reported by Udenfriend S, et al.: Fluorescamine: A Reagent for Assay of Amino Acids, Peptides, Proteins, and Primary Amines. Science Vol. 178, Nov. 24, 1972. Fluorescence of the mixture was measured in a fluorescence spectrophotometer (Perkins Elmer Model 650-10M). The instrumentation is designed quantify fluorescence for solutions. The fluorescence of gels suspended in a solution can be tested but the determination of the gel surface amine concentration is not readily ascertained.

ESCA

This analysis was performed on gels with collagen hydrolyzed from the surface. The samples were also air dried overnight and vacuum dried for six hours. The samples were analyzed in an Surface Science spectrophotometer (Mod 101). Survey scans focused on spot sizes of 1000 $\mu$m.

ATR-IR

The samples were prepared by air drying the materials overnight and then vacuum drying for six hours. The material were studied in a Perkins Elmer IR spectrophotometer (Model 1430) utilizing a ZnSe crystal for multiple internal reflectance. The range of study was from 4000 $cm^{-1}$ to 700 $cm^{-1}$.

RESULTS

Microscopy

Figure 1:
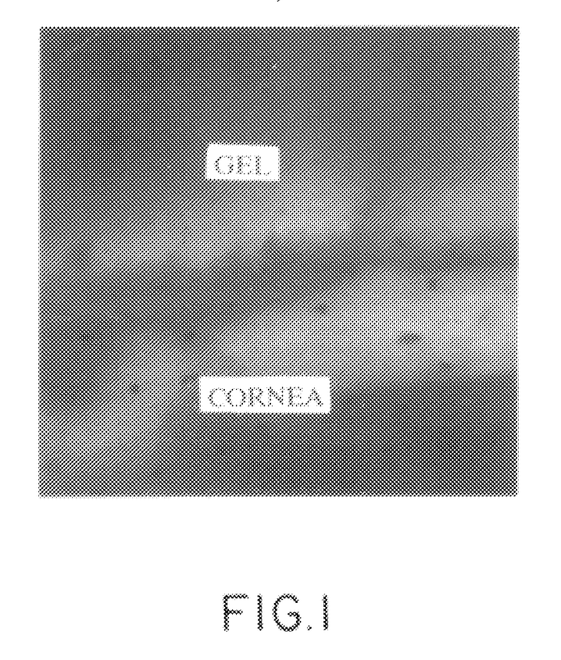
FIG. 1 is a micrograph of a 15% PEO gel adhered onto corneal tissue using 10 Mrad of electron beam crosslinking.

Initial visualization of the PEO gel/tissue interface was performed through light microscopy and SEM. Light micrographs of corneal tissue grafted onto PEO gels with a 10 Mrad dose of irradiation are shown in FIG. 1. These samples were embedded in paraffin, sectioned at 6 $\mu$m and stained with hematoxylin and eosin. The gels appear well adherent with no gaps in the interface between gel and tissue at the light microscopic level.

Figure 2:
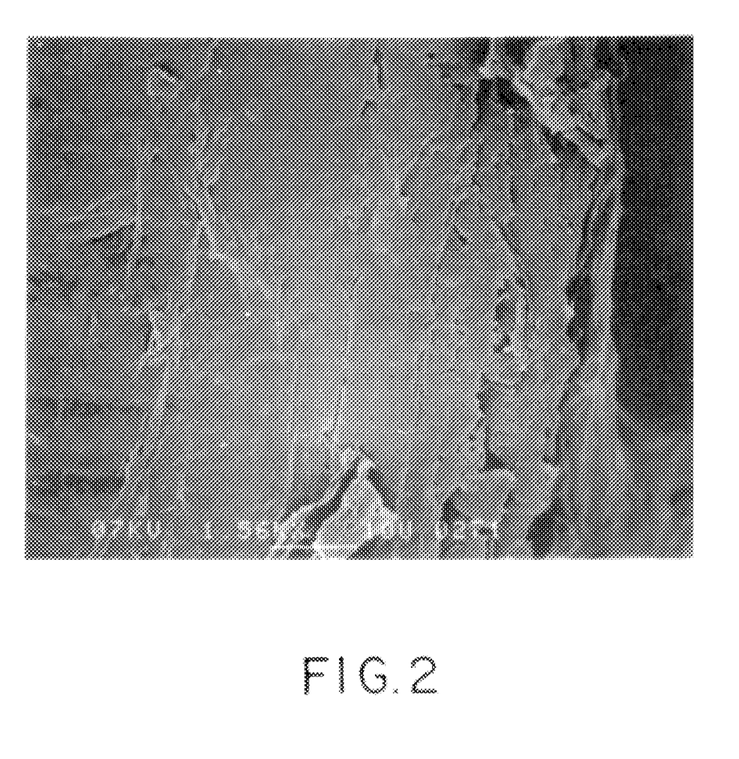
FIG. 2 is an SEM micrograph of a 10 $\mu$m layer of cornea adhered onto 15% PEO hydrogel (top view).

Scanning electron microscopy of gels grafted onto 10 $\mu$m sections of corneal tissue provided a more detailed visualization. The top view of the cut edge of the material is shown in FIG. 2. Lamellae characteristic of cornea are seen overlying the hydrogel which is beneath the tissue. One to two corneal lamellae are seen in the micrograph. Comparison with a micrograph of the typical appearance of corneal tissue, from Komai Y, Ushiki T: The Three-Dimensional Organization of the Collagen Fibrils in the Human Cornea and Sclera. Invest. Ophthal. Vis. Sci. 32:2244–2258, 1991, shows that the crosslinked corneal tissues looks the same as normal corneal tissue.

ESCA and Fluorescamine Labelling

The objective of the ESCA and fluorescamine labelling was to verify that stable covalent bonding between the gel and collagen had occurred during EII crosslinking and to characterize the nature of the bonds formed. Aqueous irradiation forms carbon radicals on the amino acid which recombine with other carbon radicals produced on the polymeric network to form PEO collagen crosslinks. The carbon-carbon bonds are very stable but peptide hydrolyzable with acidic media. Only the carbon-carbon bonds remain intact following hydrolysis of these peptide bonds, leaving single amino acids bound to the PEO network via carbon-carbon bonds. Control surfaces were prepared by carrying out the same hydrolysis reaction in the presence of corneal collagen which was simply placed in contact with the gel, but which had not been crosslinked.

ESCA was used to investigate the presence of residual amino acids on the surface. Survey scans of materials included those for PEO gels alone and with grafted collagen removed. The survey scan showed the presence of carbon, oxygen, sodium, chloride and nitrogen. The ratio of carbon to oxygen is roughly 2:1, indicative of the high concentration of PEO on the surface. Nitrogen is assumed to arise from the presence of amino acids bound to the surface of the hydrogels. PEO crosslinked without collagen was also exposed to the hydrolysis. After washing, these gels do not exhibit the presence of nitrogen on the surface.

Fluorescamine labelling was used to assay for nitrogen present in amino acid form. Primary amine-fluorescamine conjugates fluoresce at 475 nm with excitation at 390 nm. Fluorescence was noted for those collagen grafted gels which were treated hydrolytically. PEO gels not crosslinked to collagen did not fluoresce.

Surface Infrared Spectroscopy

Surface analysis for functional groups was performed with ATR-IR on PEO gels with collagen removed by acid hydrolysis. Three control spectra were obtained for comparison: (1) Linear PEO (100K), (2) Collagen Type I, and (3) Pure PEO gel treated with acid hydrolysis. Characteristic absorption frequencies are shown in Table 1, as shown in Yannas I V: Collagen and Gelatin in the Solid State. J. Macromolecular Sci.—Revs. Macromol. Chem., C7(1) (1972) p. 49–104.

The collagen material gave an IR spectrum with characteristic peaks at 1640 $cm^{-1}$ and 1540 $cm^{-1}$ due to Amide I and Amide II bands. This compares identically with published data for collagen, Weetal (1975). The non-crosslinked linear PEO shows characteristic absorption peaks of C—H vibrations and the distinctive peak at 1080 $cm^{-1}$ due to the C—O ether linkages, Vandeberg J T (editor): An Infrared Spectroscopy Atlas for the Coating Industry. Federation of the Society for Coating Technologies, Philadelphia, Pa.

(1980). Electron beam crosslinked PEO shows the appearance of carbonyl and carboxyl functionalities at 3080 cm$^{-1}$ and 1535 cm$^{-1}$, Dennison K A: Radiation Crosslinked Poly(ethylene oxide) Hydrogel Membranes. PhD Thesis, MIT (1986).

TABLE 1

Characteristic Infrared Absorption Frequencies

| Bond | Wavenumber (cm$^{-1}$) |
| --- | --- |
| O—H | 3450–3400 |
| N—H (stretch) Overtone of Amide II | 3330–3290 |
| C—O (Amide I) | 3060–3100 |
| N—H (deformation) C—N (Amide II) | 1550–1535 |
| CH$_2$ Scissor | 1445–1455 |
| CH$_2$ Wag | 1340–1310 |
| CH$_2$ Stretch N—H Deformation (Amide III) | 1270–1230 |
| C—O Ether linkages and Hydroxyl | 1085–1075 |

IR spectra elicited for collagen on PEO gel confirms the presence of collagen on the surface of the gel. After the hydrolytic removal of collagen from the surface of the gels, the IR spectra regressed to a form similar to that of non-grafted PEO gels also treated hydrolytically. The peak at 1085–1075 cm$^{-1}$ identifies the major presence of PEO on the surface. The significant differences in the infra-red spectrum of pure crosslinked PEO with gels which had collagen hydrolytically removed are the increased absorption at the Amide I, Amide II regions, and below 1000 cm$^{-1}$, Silverstein, et al., "Spectrometric Identification of Organic Compound", 4th Ed. John Wiley and Sons, Inc. New York (1981). There is a higher absorption for gels grafted onto collagen with 10 Mrad doses than those for 7.5 Mrad doses indicating a dose response behavior.

Light micrographs showed the material to be unified bilayer materials with no discernable gaps at the interface. SEM shows that corneal tissue adhered onto the gels appears similar in architecture to normal tissue although further studies of tissue architecture are needed. By hydrolyzing the collagen off of the grafted PEO gels, only amino acids covalently bound to the gels were left on the surface. ESCA survey scans identified the presence of nitrogen on the surface of the gels. Furthermore, fluorescamine labelling of these gels identified the nitrogen as present in amine form. Although the presence of amino acids was verified with labelling, the number and type of amino-acids present was not readily ascertained. To complement these surface studies of the gel/collagen interface ATR-IR was used. The IR spectra also identified the presence of amino-acids with accentuation of bands at 1640 cm$^{-1}$ and 1540 cm$^{-1}$. In addition, the IR spectra identified a higher number of amino-acids covalently bound as a function of crosslinking dose.

Because complete epithelialization of the surface of the device is needed for long-term clinical function, a material which provides both a suitable surface for cell attachment and which allows for diffusion of nutrients from the anterior chamber of the eye to the surface of the prosthetic cornea was developed. Previously, electron induced covalent bonding of collagen to non-ophthalmic medical materials has been performed in an effort to increase the adherence of collagen, as reported by U.S. Pat. No. 3,955,012 (May 4, 1976) by Okamura S and Hino T: Silicone Rubber Coated with Collagen. Strong, stable adhesion of the corneal tissue layer to the gel is necessary so that the synthetic surface modification for biocompatibility is permanent. The stability of covalent bonding further ensures that the thin-layer tissue will remain on the synthetic material truly imparting the corneal tissue biological activity, as reviewed by Brightbill F S, Corneal Surgery: Theory, Tissue and Technique. The C. V. Mosby Company St. Louis, Mo. (1986), and strength to the implant.

These results demonstrate that collagen can be covalently linked to PEO hydrogels by EII-crosslinking, and that the bonds are stable toward acid hydrolysis. Furthermore, the collagen retains features of its native architecture and may be a more suitable substrate for corneal epithelial cell growth than other formulations of collagen.

EXAMPLE 2

Synthesis and Physical Characterization of Hydrogel Bonded to Collagen by EII

The simultaneous synthesis and chemical attachment of hydrogels onto a collagenous matrix is performed using an electron beam source, a collagen substrate layered onto the bottom of a container (Fluoroware, H22 Series), and an aqueous solution of 5.25% polymer covering the collagen substrate. The assembly (container, collagen, and solution) are irradiated with doses of 10 Mrads at a rate of up to 100 Mrad/sec. The resulting hydrogels grossly appear to be optically clear, firmly gelled, and adherent to the collagen.

Substrates of corneal tissue, 70% collagen (pre-extracted) and 100% collagen (extracted), are made into sheets from freshly enucleated bovine (calf) corneas. The collagenous substrate is placed in a freezing microtome, and sheets of tissue, 10 mm in diameter, can be cut into thicknesses varying from 20 microns or larger. The semi-rigid collagen sheets are placed into 25.4 mm diameter air-tight polypropylene dishes. After lyophilization, substrates are kept in a vacuum at 0° C. until use.

Aqueous solutions of polyethylene oxide (PEO) or polyvinyl alcohol (PVA) are used in the synthesis since hydrogels made of these polymers are well-characterized (see Table 2). The polymer solutions are placed over the collagen sheets in polypropylene dishes which are now ready for electron beam irradiation. The high voltage source of electron irradiation is supplied by a Van de Graft generator. The irradiation area is 1 cm$^2$. This machine is capable of delivering dose rates of up to 10 Mrad/sec to samples conveyed along a belt at 1 cm/sec. Gelling and crosslinking is virtually instantaneous in these systems. After irradiation, the samples are ready for further analysis.

TABLE 2

PEO/PVA Hydrogel Characteristics

| Characteristics | Poly(ethylene oxide) | Poly(vinyl alcohol) |
| --- | --- | --- |
| Ultimate strength | app. 25 psi | 180–400 psi |
| Polymer concentration | 5–25% | 10–25% |
| Permeability* | | |
| albumin | negligible | 7.6–3.18 |
| inulin | 4.1–2.8 | not available |
| Clarity | + | + |
| E-beam crosslinked | + | + |

*cm sec × 10$^{-6}$

Important factors in polymer-collagen crosslinking are polymer concentration, polymer morphology, irradiation dose, dose rate, and depth of penetration. By varying the parameters stated above, polymer-collagen interfacial crosslinks can be varied.

Interfacial Analysis

In order to observe the interface with surface analysis techniques, the collagen is removed by enzymatic and oxalic acid degradation, using the method of Pietrucha (1986). This preserves the gel structure while still hydrolyzing the protein into amino acids. Collagen is first cleaved by collagenase, then lysed into peptides by non-specific protease and finally hydrolyzed into amino acids (AA) by oxalic acid. Proteolytic degradation removes all AAs except those which are chemically bonded onto polymer chains of the hydrogel. Non-extracted amino-acids (from collagen) are considered covalently linked onto the hydrogel surface and are detectable by surface analytical techniques and amino acid labeling techniques. The amino acids which are most highly reactive to participation in crosslinking are shown in Table 3.

TABLE 3

Reactive Amino Acids in Collagen

| Amino Acid | No. of AA 1000 residues | $k_2 \times 10^8$ (mol$^{-1}$sec$^{-}$) |
| --- | --- | --- |
| Proline | 126 | 2.0 |
| HydroxyProline | 92.1 | 3.0 |
| Arginine | 49 | 10.0 |
| Phenylalanine | 14.2 | 7.0 |
| Histidine | 5.4 | 70.0 |
| Tyrosine | 3.6 | 10.0 |

Interface topology is studied with screening methods such as scanning electron microscopy (SEM). The architecture of hydrogels in the hydrated state is preserved by certain processing methodologies or use of environmental scanning electron microscopy. SEM-identified interface topology will verify any auxiliary mode of attachment such as mechanical intercalation of hydrogel into the collagen matrix. This may show up as roughness in the hydrogel interface.

A quantitative surface analysis technique is electron spectroscopy for chemical analysis (ESCA). Immobilized AAs analyzed in ESCA provide binding energy signals of nitrogen in addition to polymeric carbon and oxygen from PEO. The nitrogen (N1S) peaks from ESCA can allow quantification of the amount of elemental nitrogen on the top 50 angstroms of the surface. This is an indirect measure of the quantity of surface bound AAs. ESCA can analyze surface areas from 5 mm to 150 micrometers to a depth of 1–20 atomic layers. The precision of elemental analysis varies from 10–20%. Elemental detection limits are from 0.1–1.0%. The quantity of bound AAs and its relationship to polymer concentration, irradiation dose, dose rate, and irradiation depth of penetration is to be ascertained.

An additional method of studying interface amino acids bound to synthetic polymer is to label these amino acids with fluorescent or colored labelling molecules. Amino acid labelling reagents have been used classically to label the amino termini of peptides being sequenced. Some of these labelling reagents are: ninhydrin, fluorescamine, dansyl chloride, and orthophthaldiol aldehyde (OPT), which can be obtained from Sigma Chemical Co., St. Louis, Mo. The labelling protocols which use these reagents can detect nanogram to picogram quantities of the amino acids. Also, the particular absorbance characteristic of labelled amino acids allow the identification and quantification of particular amino acids. Polymer/amino acid conjugates can be acid hydrolyzed from the hydrogel network and spectrophotometrically quantified.

In order to determine sites of activation, separation of the AAs can be performed with high pressure liquid chromatography. This technique can be used to find attachment sites of polymer to AAs. Standards for such analyses can be made by electron beam irradiation of AA homopolymers within polymeric solutions. Standard amino acid homopolymers linked to polymer chains are hydrolyzed into single AAs. The networks and bound amino acids are washed to remove any residual amino acids not bound. The polymeric network is then hydrolyzed to free amino acid/monomer dimers. These dimers can be labelled with colored or fluorescent derivatives and separated through HPLC. Comparison of labelled elution fractions of samples against standard elution profiles derived from homopolymeric amino acids allows identification and quantification of modified AAs. Some irradiation modification of amino acids is expected but the majority of radical site generation will be on the alpha carbon of the peptide chain.

Light microscopy is used to analyze the histologic appearance of the collagen in the composite material. Immunofluorescence techniques are highly sensitive in antigenically determining biological changes. Antibodies to specific portions of the collagen type I molecule are commercially available. To perform immunofluorescent analyses, composites are sectioned and stained with the appropriate antibodies. Changes in the staining properties are used as a indirect measure of changes in the biological character of fibrillar collagen.

An in vitro enzymatic degradation assay can allow determination of the process induced changes which alter the proteolytic susceptibility of the collagen in the composite material. Unmodified collagen is not susceptible to non-specific proteases and mildly sensitive to mammalian collagenase. Test materials are incubated in a particular enzyme for 20 hours and the amount of hydrolysis is compared to that of corneal collagen. Differences in degradation rate between hydrogel/collagen composites and cornea can signal changes induced by the process of composite synthesis.

Attenuated total reflection Fourier transform infra-red spectroscopy (ATR-FTIR) utilizes infrared absorption to observe the chemical functionalities at a surface. This technique is not a true surface analytical technique although it penetrates the surface of the material to a depth of approximately one micron. It has been used to observe the surfaces of fibrillar collagen and gelatin. The ability of ATR-FTIR to determine fingerprint spectra of collagen allows one to follow the fundamental chemical changes induced in collagen due to irradiation induced crosslinking.

EXAMPLE 3

Analysis of Biological Surface Activity and Growth of Corneal Epithelial Cells Onto Composite Epithelium formation was examined following surgical implantation of the composite hydrogen through organ culture of rabbit cornea. The ability of the hydrogel to support the outgrowth of epithelial cells in a physiologic fashion, i.e., from the remaining corneoscleral rim, was demonstrated by placing the entire cornea into culture. Tissue explants were also studied to evaluate the migration and growth potential of corneal epithelial cells on the lenticule. Tissue explants provide cells which closely resemble normal cell populations in the body. In the assay, corneal tissue is placed epithelial side down on the lenticule, so that donor corneal epithelium is in direct contact with the adherent corneal stromal layer of the lenticule. Epithelial cells migrate off the tissue explant and onto the lenticule surface. Subsequently, the cells multiply and form an epithelium. Physiologically, corneal epithelial cell migration is important in normal healing. When the cornea is injured during surgical procedures, the regrowth of the epithelial layer is typically the limiting factor in healing, and the return of function is dependent upon the regeneration of a normal epithelium.

Adhesion of stratified epithelium to the underlying stroma is ultimately dependent upon the generation of numerous subcellular components in the basal layer, including hemidesmosomes, the basal lamina, and anchoring fibrils. Sipehia, et al., *Biomat., Art Cells, Art Org.* 18(5), 643–655 (1990). Studies have shown that compared with successful epikeratoplasty implants, implants that fail are found to have a decreased number of hemidesmosomes, a decreased area of basement membrane, and a decreased percentage of basement membrane area occupied by hemidesmosomes. In addition, irregularities and duplications of the basement membrane have been noted, as well as a diminished penetration into the corneal stroma by anchoring fibrils in those lenticules that ultimately fail, as reported by Azar, et al., *Ophthal.* 109, 1279–1284 (Sep. 1992). To date no one has demonstrated the presence of hemidesmosomes in in vitro studies of corneal epithelial migration on synthetic materials. Therefore, in this study, transmission electron microscopy was used to search for evidence of basal specialization obtained by migrating epithelial cells on our lenticule.

Materials and Methods

Characteristics of the Hydrogel: The implant under study was a composite of 2% polyethylene oxide hydrogel, 150 $\mu$m in thickness, with a 50 $\mu$m layer of native corneal tissue covalently attached. It was sterilized with 70% ethanol prior to implantation.

Organ Culture: New Zealand White rabbits were sacrificed with an overdose of sodium pentobarbital administered intravenously. The eyes were immediately enucleated and transported on ice in a moist chamber to the laboratory. Each globe was rinsed for 1 min. with normal saline containing 200 $\mu$g/ml polymyxin B sulfate and prepared and draped in a sterile fashion. An epithelial wound was created by marking an area on the central cornea with a 5 mm trephine cut to a depth of approximately 1 mm and removing the encircled epithelium by blunt dissection with a Paton spatula. The debrided surface was irrigated with sterile phosphate buffered saline (PBS). Next a peripheral lamellar dissection was performed at the bottom of the trephine cut with an angled lamellar dissector extending to the limbus, as described by McDonald, et al., Kaufman, 823–845 (1988). Using Polack forceps and a sterile cotton swab the implant (previously cut to a diameter of approximately 10 mm) was placed on the denuded cornea and the edges were tucked below the recipient lip so that they lay in the peripheral lamellar keratotomy created by the lamellar dissector. Due to the large area of lenticule lying within the circular keratotomy, no sutures were required to mechanically secure the lenticule. During surgery, the cornea was periodically moistened with sterilized saline solution containing polymyxin B. The cornea was then carefully excised, including a scleral rim of 2 mm, and the explant was brought into culture by transfer into a 6 well plate (Costar) containing sufficient media to cover the tissue. The media was prepared from keratinocyte serum-free media (Gibco) supplemented with epidermal growth factor (2.5 $\mu$g), BPE (25 mg), L-glutamine, and gentamicin (pento 20 $\mu$g). The plates were then incubated at 37° C. and 5% $CO_2$ for 5 to 7 days with a media change after three days.

Following the incubation period, the eyes were immersed in 10% paraformaldehyde for fixation. The corneas were imbedded in methacrylate and three $\mu$m cuts were made by microtome for histologic examination. The sections were stained with hematoxylin-eosin (H&E) and toluidine blue for light microscopy and evaluation of cell morphology and differentiation.

Tissue Explant Studies: New Zealand white rabbits were killed with an overdose of sodium pentobarbital administered intravenously. The corneas were excised and rinsed twice in sterilized PBS. The endothelial cell layer of each cornea was removed with a sterile cotton swab and four circular disc-shaped buttons (5 mm in diameter) were obtained by sterile trephin from just within the corneoscleral junction. The buttons were placed, epithelial side down, on the synthetic lenticule in a 6 well tissue culture plate and covered with 3.0 ml of NBK-5A media. The culture dishes were allowed to incubate at 37° C. and 5% $CO_2$, with a media change after 2 days. After 7 days, the lenticules were immersed in half-strength Karnovsky's glutaraldehyde-formaldehyde fixative, post-fixed in 2% osmium tetroxide, stained en-bloc with uranyl acetate, dehydrated and embedded according to standard technique. Semi-thin sections were cut and stained with para-phenylenediamine (PPDA) for phase contrast microscopy. Ultra-thin sectioned and uranyl acetate/lead citrate stained tissues were viewed with a Philips 410 transmission electron microscope.

Results

Organ Culture: Histologic examination revealed migration of epithelial cells onto the hydrogel within a seven-day period. A confluent layer of epithelial cells was observed over the implant over time with scattered areas of two cell layered stratification.

Tissue Explant Studies: Transmission electron microscopy (TEM) revealed well-adherent, healthy appearing epithelial cells attached to the stromal layer of the lenticule. Numerous mitochondria could be seen to predominate in the basal layer.

Purpose

The goal of this project is to evaluate epithelial cell interactions with a synthetic material designed for keratoprostheses.

Methods

Composite hydrogels are hybrid materials made of corneal stromal tissue and a synthetic polyethylene oxide hydrogel base. The hydrogel is coated with a 40 $\mu$m layer of corneal stromal tissue bound to the surface of a hydrogel. Epithelial wound closure was evaluated on these materials using a two chamber cell culture system meant to mimic the clinical situation. The hydrogels are suspended between a humidified air chamber (5.5% $CO_2$) and a serum free media chamber. Epithelial cell migration and proliferation onto the material is observed daily via phase contrast microscopy. Samples are processed by immunohistochemistry to determine production of basement membrane proteins.

Results

Epithelial cells from corneal tissue explants readily adhere and grow to confluence over the composite hydrogel surface. Three millimeter diameter wound areas are epithelialized within four days after an initial two day lag period. Histological results show a multilayered epithelium 2 to 3 cell layers thick. By week 8, immunohistochemistry demonstrates the deposition of a continuous basal layer of laminin.

Conclusions

Composite hydrogels of stroma and synthetic hydrogel support epithelial cell attachment and growth to confluence. Laminin deposition and multilayer stratification demonstrates the ability of the materials to support regeneration of epithelial characteristics.

Modifications and variations of the present method and materials for forming and using epikeratoprostheses will be obvious to those skilled in the art from the foregoing detailed description. Such modifications and variations are intended to come within the scope of the appended claims.

We claim:

1. A method for making an implantable composite keratoprosthesis comprising placing corneal tissue in a mold having a corneal implant shape, placing in contact with the corneal tissue a biocompatible hydrogel between approximately 50 and 100 microns in thickness, placing between the corneal tissue and hydrogel a polymerizable polymeric solution, and polymerizing the polymeric solution to chemically bond the hydrogel to the corneal tissue to form a keratoprosthesis, wherein upon implantation the corneal tissue abuts epithelial cells surrounding the keratoprosthesis.

2. The method of claim 1 wherein the corneal tissue is between approximately 10 and 50 microns in thickness.

3. The method of claim 1 wherein the hydrogel is selected from the group consisting of hydroxyethylmethacrylate, polyethylene oxide, polyvinyl alcohol, polydioxolane, poly(acrylic acid), poly(acrylamide), and poly(N-vinyl pyrilidone).

4. The method of claim 1 wherein the hydrogel is bound to the corneal tissue by electron irradiation induced polymerization of the polymeric solution.

5. The method of claim 1 wherein the corneal tissue is lyophilized.

6. The method of claim 1 wherein the hydrogel is adhered to the corneal tissue by absorption of the polymeric solution into the tissue prior to polymerization of the polymer.

7. The method of claim 1 further comprising trimming the corneal tissue of the implant to provide the desired optical properties.

8. A method for making an implantable composite keratoprosthesis comprising providing a hydrogel formed in a shape suitable for a corneal implant;

providing corneal tissue in close proximity to the hydrogel;

wherein the hydrogel is between approximately 50 and 100 microns in thickness and the corneal tissue is between approximately 10 and 50 microns in thickness, providing a liquid polymer solution between the hydrogel and the corneal tissue; and adhering the corneal tissue to the hydrogel by polymerizing the polymer solution.

9. The method of claim 8 wherein the hydrogel and the polymer solution are selected from the group consisting of hydroxyethylmethacrylate, polyethylene oxide, polyvinyl alcohol, polydioxolane, poly(acrylic acid), poly(acrylamide), and poly(N-vinyl pyrilidone).

* * * * *